(12) United States Patent
Bauch et al.

(10) Patent No.: US 8,209,438 B2
(45) Date of Patent: Jun. 26, 2012

(54) COMPUTER NETWORK SYSTEM AND METHOD FOR OPERATING A NETWORK SYSTEM SCREEN SHOT AND SOURCE SHOT CONTROL

(75) Inventors: Thomas Bauch, Bergkirchen (DE); Peter Krüger, Kirchheim (DE); Gerhard Lang, Munich (DE)

(73) Assignee: Brainlab AG, Feldkirchen (DE)

(*) Notice: Subject to any disclaimer, the term of this patent is extended or adjusted under 35 U.S.C. 154(b) by 686 days.

(21) Appl. No.: 11/677,276

(22) Filed: Feb. 21, 2007

(65) Prior Publication Data

US 2007/0198001 A1 Aug. 23, 2007

Related U.S. Application Data

(60) Provisional application No. 60/745,029, filed on Apr. 18, 2006.

(30) Foreign Application Priority Data

Feb. 21, 2006 (EP) ..................................... 06003509

(51) Int. Cl.
*G06F 15/16* (2006.01)
*A61B 17/00* (2006.01)

(52) U.S. Cl. .............................. 709/250; 709/249; 606/1

(58) Field of Classification Search .......................... None
See application file for complete search history.

(56) References Cited

U.S. PATENT DOCUMENTS

| 5,036,315 | A | * | 7/1991 | Gurley ........................... 715/733 |
| 5,721,842 | A | * | 2/1998 | Beasley et al. ................. 709/204 |
| 5,788,688 | A | | 8/1998 | Bauer et al. |
| 6,117,127 | A | | 9/2000 | Helmreich et al. |
| 6,701,380 | B2 | * | 3/2004 | Schneider et al. ............. 709/250 |
| 6,928,490 | B1 | | 8/2005 | Bulcholz et al. |
| 6,957,287 | B2 | * | 10/2005 | Lou et al. ......................... 710/72 |
| 7,401,116 | B1 | * | 7/2008 | Chalfin et al. ................. 709/203 |
| 2002/0165922 | A1 | | 11/2002 | Wei |
| 2003/0171740 | A1 | | 9/2003 | Stiller et al. |
| 2003/0189581 | A1 | | 10/2003 | Nasoff et al. |
| 2004/0116908 | A1 | * | 6/2004 | Birkenbach et al. .............. 606/1 |
| 2004/0260764 | A1 | | 12/2004 | Witchel |

FOREIGN PATENT DOCUMENTS

| EP | 1 433 432 | 12/2002 |
| EP | 1 394 717 | 3/2004 |
| EP | 1 433 432 | 6/2004 |
| WO | 02/080556 | 10/2002 |

OTHER PUBLICATIONS

Nadeau et al., "Network Video Device Control", pp. 299-306, 1992.

(Continued)

*Primary Examiner* — Wen-Tai Lin
(74) *Attorney, Agent, or Firm* — Renner, Otto, Boiselle & Sklar, LLP

(57) ABSTRACT

A computer network system includes a controlling PC, at least one controlled PC controllable by the controlling PC via a data connection including a network, at least one central terminal having a display, and a video router. The video router is operatively coupled to each of the at least one controlled PCs and the at least one central terminal display and operative to transmit video or monitor signals from each of the controlled PCs to the at least one central terminal display.

23 Claims, 3 Drawing Sheets

OTHER PUBLICATIONS

Herron et al., "The minimally invasive surgical suite enters the 21$^{st}$ century", 2001, Surgical Endoscopy, Ultrasound and Interventional Techniques, pp. 415-422.

Fisher et al., "Development of an Access-by-the-Internet Control Laboratory", Dec. 2001, pp. 2827-2832.

European Search Report for corresponding European Application No. 06003509.4 dated Mar. 1, 2007.

European Search Report for Application No. 10175007.3 dated Nov. 8, 2010.

European Search Report for Application No. 06003509.4 dated Oct. 19, 2006.

* cited by examiner

COMPUTER NETWORK SYSTEM AND METHOD FOR OPERATING A NETWORK SYSTEM SCREEN SHOT AND SOURCE SHOT CONTROL

RELATED APPLICATION DATA

This application claims priority of U.S. Provisional Application No. 60/745,029 filed on Apr. 18, 2006, which is incorporated herein by reference in its entirety.

FIELD OF THE INVENTION

The present invention relates to computer network systems and, more particularly, to a network connection for connecting several electronically controlled medical devices so that they may be controlled via a central terminal and display. The invention also relates to a method for obtaining screen shots and source shots.

BACKGROUND OF THE INVENTION

It is known from the Microsoft Windows remote desktop system that the desktop of a first PC can be transferred over a network to a second PC. On the second PC, a user can use a keyboard and a mouse to control the first PC. This input (i.e., keyboard and mouse control) is also transferred over the network back to the first PC.

Furthermore, a Keyboard-Video-Mouse switch (KVM-switch) is known, wherein a central monitor, keyboard and a mouse can be connected to the KVM switch, and two or more PCs also can be connected to the KVM switch. The KVM switch can be used to switch the keyboard, mouse and monitor between the different PCs. As a result, each connected PC can alternatively be seen and controlled over the central monitor/keyboard/mouse. The video and input signals can be directly transferred over their normal cables, such as RGB-cable or PS/2-cable.

EP 1 433 432 A1 corresponding to US 2004/0116908 A1 discloses a device for coupling at least two medically applicable instruments to at least two control apparatuses. The device can include a central control unit coupled to input or output connections of the at least two control apparatuses. The central control unit can include at least one processor that receives output signals from the at least two control apparatuses and converts the output signals into a unified format. At least one processor can receive inputted control signals, convert the control signals into formats corresponding to the respective at least two control apparatuses, and transfer the converted control signals to the at least two control apparatuses to control the at least two medically applicable instruments.

U.S. Pat. No. 5,788,688 discloses a surgeon's command and control system including an independent personal computer based electronic control unit. The control unit unifies various pieces of equipment currently found in an endoscopic surgical suite into a surgeon centered system. The system utilizes programmed software that can simplify equipment management tasks that currently encumber the surgeon and operating room staff. The surgeon's command and control hardware centers around the personal computer communicating with a sterile control panel located at the surgeon's operating station. A frame store card serves as an electronic pallet to compose and superimpose graphic images onto a surgical image transmitted from an endoscopic camera for display on a heads-up display monitor and the surgical operating station.

U.S. Pat. No. 6,117,127 discloses a medical system work station for open or minimally invasive surgery that has a holder tray and at least one terminal unit for handheld instruments of one or more medical devices, at least one equipment center, spatially separated from the terminal unit, for accepting non-manipulated components of the medical devices, and at least one connection unit that connects the terminal unit and the equipment center with one another.

U.S. Pat. No. 6,928,490 B1 discloses a networking infrastructure for an operating room, comprising a plurality of medical devices, wherein each device is connected through a single communication channel to the network, and each device may be controlled through a local interface, or through a remote interface available through the network. Furthermore, the networking infrastructure operates in robust manner with respect to the removal of a communication channel to the network associated with the removal of medical device from the network, or with respect to the addition of a communication channel to the network associated with the addition of a medical device to the network.

SUMMARY OF THE INVENTION

A computer network system includes at least one and preferably two or more controlled computers, which are hereinafter designated as controlled PCs. The controlled PCs can include a software, control or computer system for controlling a respective device, preferably a medical device. The device also can be or is controlled by another and preferably remote controlling computer or PC, wherein the remote controlling PC may be connected to the controlled PC over a network. In general, a network as used herein can include every data connection between two computers or PCs and can be a standard network or any other data connection such as, for example, a serial or parallel data connection or cables. The computer network system can further include a controlling computer hereinafter referred to as a controlling PC, which may be connected via the network (e.g., Ethernet or the like) to the controlled PCs to transmit control commands from the controlling PC to the controlled PCs. Furthermore, at least one central terminal display can be provided, which may be connected (preferably directly connected) to the controlling PC. The central terminal enables a user to control or operate a device, such as a PC, for example, wherein controlling or operating the device may be accomplished via user input (e.g., keyboard, mouse, touch screen, etc.). Preferably, a single video routing hardware is provided that can be connected to each controlled PC so as to receive a monitor or video signal from each controlled PC. The video routing hardware also can be connected to the at least one central terminal display to transmit a monitor or video signal (e.g., to display the screen content of the controlled PC on the central terminal), preferably of the same quality and resolution as that received from one or more of the controlled PCs.

Thus, by using different channels for video and input data, the advantages of the KVM switch and remote desktop technologies can be combined. Video routing using a video router instead of transmitting the video signals over the network provides superior image quality and performance. The input transfer over a data connection provides broad compatibility between different devices that cannot be achieved using a conventional KVM switch system. By separating the network or data transfer system into a network system for transferring commands on the one hand and into a video router for transmitting monitor or video signals on the other hand, the original image quality and resolution provided by each of the controlled PCs, which can be the control devices of medical instruments, such as imaging devices or laparoscopic devices, can be retained and is not impaired while being transmitted to the central terminal display.

In case of using a touch screen as central terminal, it is even possible to control different devices with incompatible touch screen drivers, because the central touch screen is never directly connected to the controlled PC, but to a controlling PC which can convert command signals from the central terminal touch screen into respective different command signals of the controlled PCs.

It is also possible to simultaneously control a PC from different terminals. The video routing hardware can distribute the video signal to more than one terminal and all these terminals can display and operate the same PC simultaneously.

The possibility of controlling different medical devices from one or more terminals eliminates the need for the surgeon or assisting personal to manipulate and control each single device through its own control screen, buttons or switches. As a result, it is not necessary to access the respective medical device, which can be located at a remote location from the surgeon or assisting personal, so that the time-consuming and sometimes cumbersome procedure for manipulating and controlling each separate medical device is no longer necessary. Further, it may also allow to completely eliminate the screen and control means of the controlled PC, which simplifies the system set-up.

Medical devices that do not offer an option for sterile manipulation and that commonly require handling by a non-sterile assistant can be controlled in the sterile field via the central touch screen which can be provided with a sterile draping.

Since the original graphic user interface of the respective medical device can be presented to the user, and since the original video or monitor signal is directly and preferably unchanged when sent to the central terminal display, the user does not have to adapt to an additional or foreign user interface, which enhances the usability and operability of the whole computer network system. Therefore, it is not necessary to implement a mirrored user interface for every single controlled application. The controlled application does not need to support the additional control in any way, since it is not necessary to distinguish whether some input has its origin in a local keyboard, mouse or touch screen, or whether it was generated by additional software, which may be installed on each respective controlled PC and called an "input client".

Preferably, error or warning messages from at least one and preferably all integrated controlled PCs can be displayed on the central terminal. As a result, the user only has to watch a central terminal display and is not forced to look on every single screen of every separate medical device, or to switch through all devices to see if errors occurred or warnings were output. If such an error or warning message occurs, this message always can be visible on a central terminal, e.g., by displaying it in front of the actual screen, regardless which medical device or PC is currently visible.

According to a further aspect of the invention, there is provided a method for operating a network system as described above, wherein control commands from a controlling PC or controlling computer can be sent via a data connection (which can include a network) to at least one controlled computer or PC. The video or monitor signals from at least one and preferably all controlled computers or PCs are sent to a video router or video routing hardware. The video router or video routing hardware transmits these monitor or video signals to at least one central terminal screen, without using the data connection or network used for transmitting control commands between the controlling computer and the controlled computers.

Furthermore, a computer program is provided that can be loaded or running on a computer and which, when loaded or running on a computer, performs the method for operating the network system as described in this application. The computer program can be stored on a storage medium or can be a computer program product comprising such a computer program.

Thus, different PCs can be controlled over one or more central terminals. These PCs can be part of medical devices. The PCs can be operated via touch screen or keyboard and mouse. On the controlled PCs, an additional software called "Input Client" can be installed that performs the control of that PC by generating operating system input events in a similar way (e.g., touch screen drivers that generate input events). This Input Client also can display a small graphical user interface in front of all other applications on that PC. On the central terminal, the graphical user interface of the Input client can be used to switch between different controlled PCs. On the local displays of the controlled PCs, the graphical user interface of the Input Clients can display status and warning messages. Since this user interface may occlude some part of the application's user interface, it detects which application is currently visible and moves itself to a suitable position on the screen, where it does not handicap the operation of that application.

The Input Client, for example, can detect warning messages of the controlled applications and can distribute them to the Input Clients of all other integrated PCs. These integrated PCs then can display a warning to the user. The detection of such warnings from an application can be done through inter-application communication, for example, by searching operating system data structures to identify whether there is a dialog window with the text "error" or "warning" in its title or by pattern recognition to identify warnings or errors by analyzing the content that is displayed by the application.

Thus, one or more PCs can be controlled from a central terminal (e.g. touch screen or monitor/keyboard/mouse), wherein to control such a PC only the input (keyboard, mouse/touch clicks) can be transferred over a network or the like. Alternatively, any other data connections to the controlled PCs can be used, including, for example, serial or parallel cables. On the controlled PC additional software (e.g., an Input Client) can receive the input events and can translate these into normal operating system input events. The principle can be compared with a touch screen driver that generates input events from the data that it receives over the serial connection to the touch screen.

The monitor signal of the controlled PCs can be distributed by a video routing hardware (e.g., a matrix switch, video processor, etc.) to the central terminal. As a result, the operator will see the original monitor content as if he would see it using a KVM switch, but control of the devices is over a data connection that is independent from the video connection.

The input signals from the central terminals (e.g., PS/2 cables of keyboard and mouse or serial/USB cable from touch screen) can be permanently connected or transmitted to the controlling PC. The monitor input of the central monitor or touch screen can be connected to the video routing hardware. The controlling PC does not need to display any content on its own graphics output and even does not need to have a graphics output and/or display.

The operator will see the original image of the controlled PC when he operates the system. His input may be received by the controlling PC and then transferred over the data connection to the controlled PC, where the control data can be translated by the Input Client into system input events. When the operator switches from one controlled PC to another one, the controlling PC can issue a switch command to the video routing hardware. The video routing hardware will then route the video signal of the newly controlled PC instead of the signal of the formerly controlled PC to the central terminal. The controlling PC can transfer the following input to the Input Client of the newly controlled PC.

To initiate such a switching between different controlled PCs, different mechanisms can be used:
  a graphical user interface of the Input Client;
  a wireless remote control that sends switching commands to the controlling PC;
  a cable-bound remote control that sends switching commands to the controlling PC;
  switch buttons that are embedded into the monitor housing and connected to the controlling PC; and/or
  hot keys for keyboard control.

BRIEF DESCRIPTION OF THE DRAWINGS

The forgoing and other features of the invention are hereinafter discussed with reference to the drawings.

DETAILED DESCRIPTION

Figure 1:
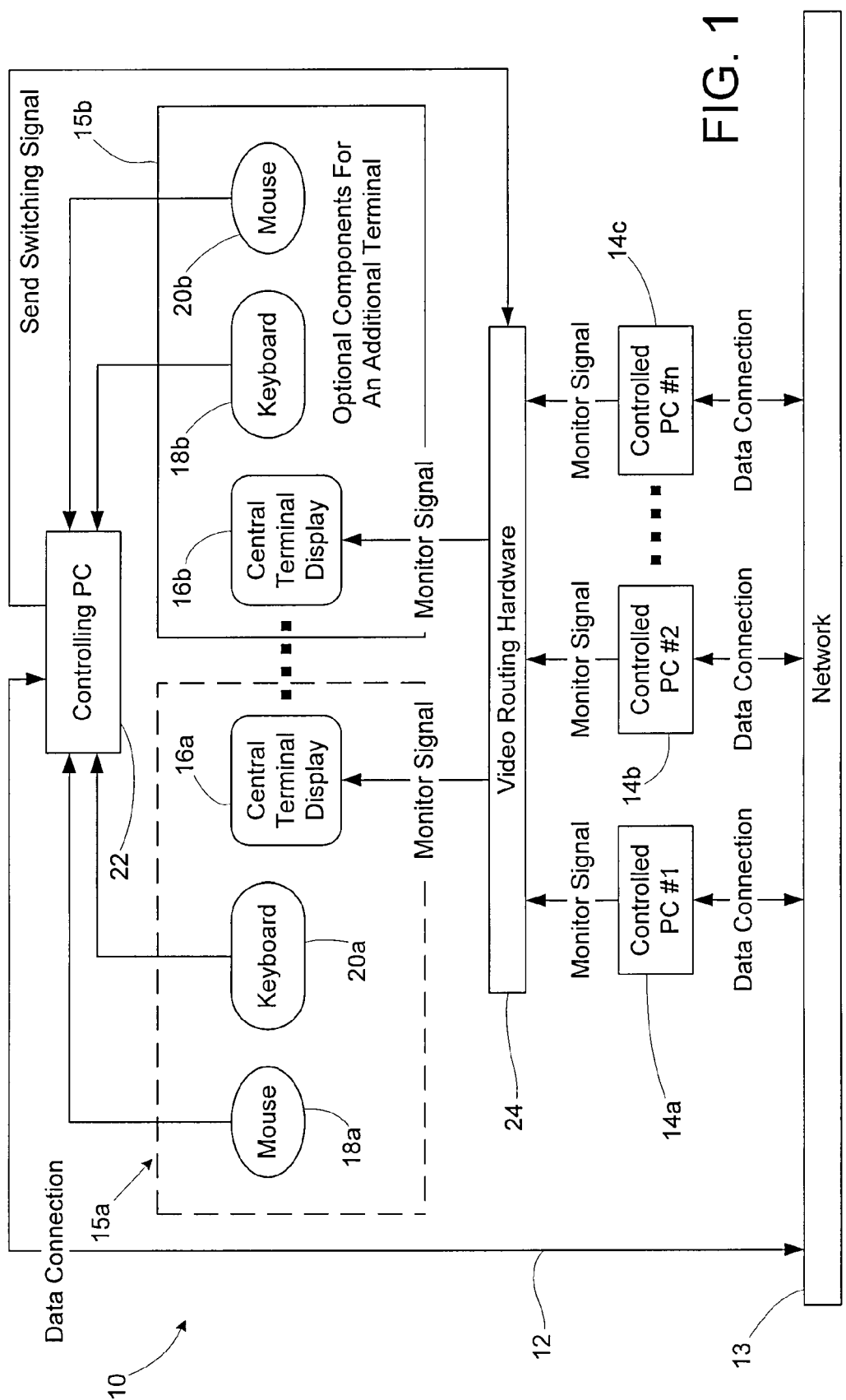
FIG. 1 is a schematic diagram of an exemplary computer network system using monitor/keyboard/mouse terminals in accordance with the invention.

FIG. 1 is a schematic diagram that shows an exemplary network system 10 that includes a data connection 12 coupled to network 13 for transferring input commands made via a keyboard and/or mouse to controlled PCs 14a-14c. In this embodiment, a central terminal 15a includes a monitor as central terminal display 16a, a keyboard 18a and a mouse 20a. The keyboard 18a and mouse 20a can be directly connected to a controlling PC 22, while the monitor 16a can be connected to video routing hardware 24. One or more optional terminals 15b can include an additional keyboard 18b and mouse 20b, which also may be directly connected to the controlling PC 22, and an additional monitor 16b can be connected to the video routing hardware 24. Each one of the controlled PCs 14a-14c can have a local monitor/keyboard/mouse or touch screen, which are not shown in FIG. 1.

Figure 2:
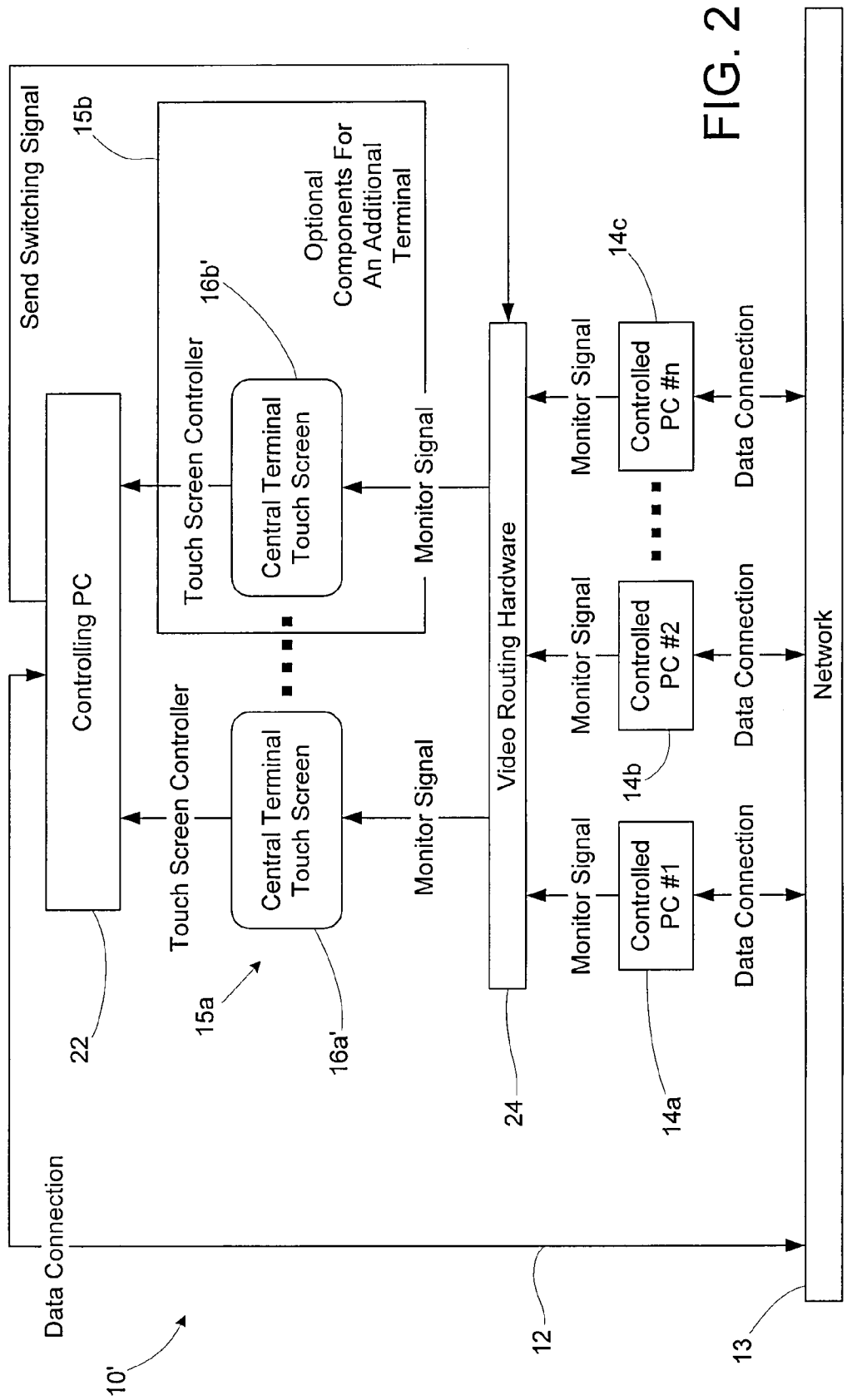
FIG. 2 is a schematic diagram of another exemplary computer network system using touch screens in accordance with the invention.

FIG. 2 is a schematic diagram of another exemplary network 10' that utilizes touch screens 16a' and 16b' instead of a monitor/keyboard/mouse for the central terminals. The monitor signal for the touch screens 16a' and 16b' can be provided by the video routing hardware 24, and the touch input entered via the central terminal touch screen 16a' can be processed by the controlling PC 22 and sent via the data connection 12 and network 13 to the respective controlled PCs 14a-14c.

Figure 3:
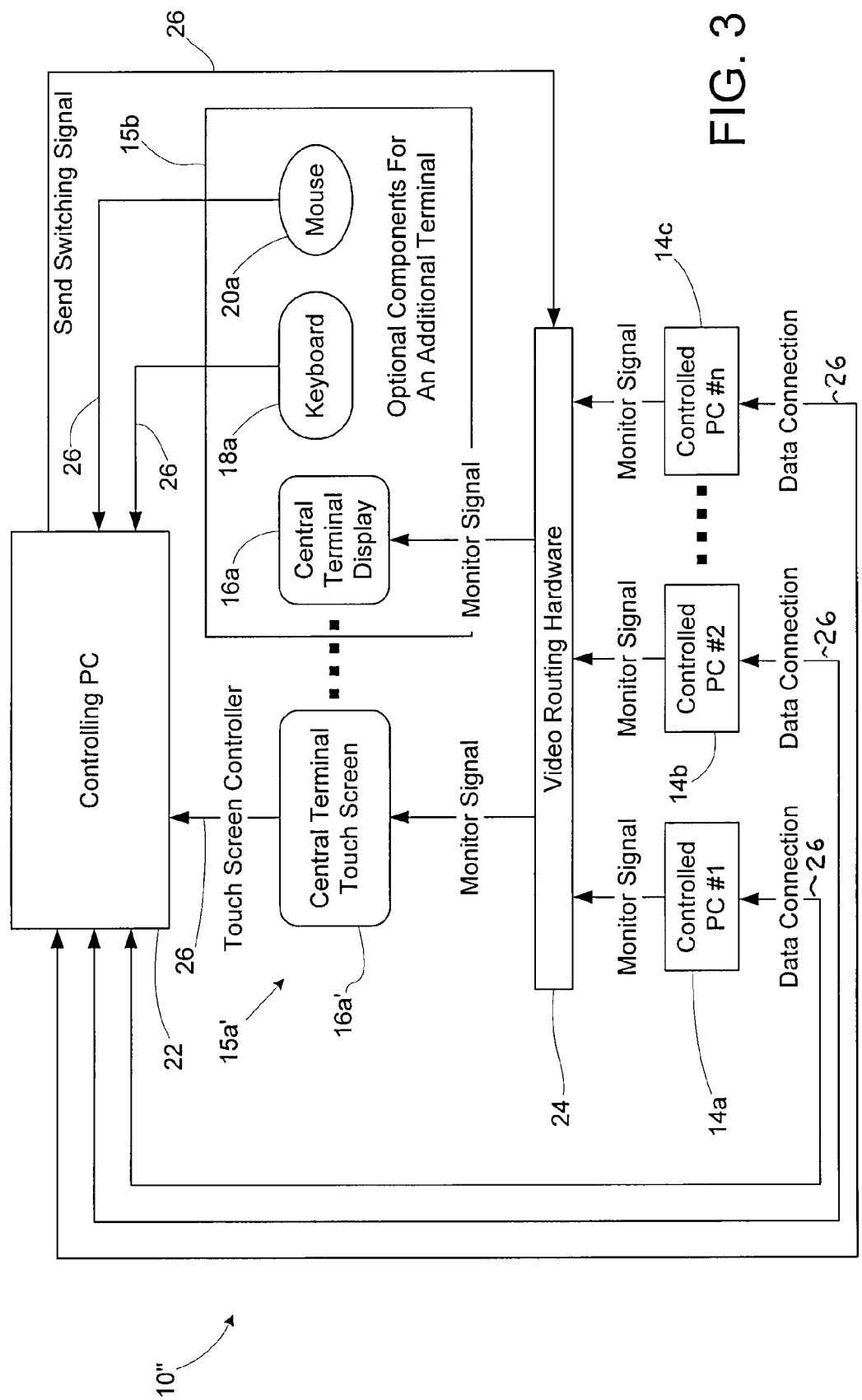
FIG. 3 is a schematic diagram of another computer network system using, in combination, monitor/keyboard/mouse terminals and touch screens in accordance with the invention.

FIG. 3 is a schematic diagram of another exemplary network 10" using monitor 16a, keyboard 18a and mouse 20a in combination with a touch screen terminal 16a' all of which can be simultaneously used. Furthermore, an alternative wiring is shown, wherein other data connections, such as for example serial cables 26, are used instead of a network 13 to transfer the input data from the central terminal touch screen 16a', keyboard 18a or mouse 20a to the respective controlled PCs 14a-14c.

An Input Client residing on the controlled PCs 14a-14c can display a small graphical user interface (GUI) in front of all other applications. This GUI may occlude some part of the application that the user wants to control. Since the occluded part can be important for the proper function of that software, the GUI can be moved to different positions on the screen. Every different application that may be controlled can have a different position on the screen where the GUI of the Input Client does not handicap the operation of that applications and where it does not cover important information displayed by the application. Such suitable positions can be configured for all applications that may be controlled. The Input Client can automatically detect which application on a controlled PC 14a-14c is currently visible and move itself accordingly to a position that is suitable for that application.

The Input Client is able to detect warning or error messages on the controlled PC. This detection can be achieved in different ways. One possibility is an inter-application-communication. In this case the application that originates the warnings is aware of the Input Client and supports the inter-application-communication. It will then directly inform the other Input Clients of the warning.

Warnings also may be detected via operating system data structures of the current window or windows. The Input Client can detect every new window that is opened and can analyze whether the window displays some warning or error information. This can be achieved, for example, by testing whether the window title contains the word "error" or "warning".

Another way to detect warning or error conditions is via pattern recognition. The Input Client can periodically analyze the screen content of its PC. If a content is recognized that is known as a warning/error condition, the Input Client can detect and forward such a condition. The Client can be trained by the user which graphical content represents such conditions.

When a warning or error condition is recognized, the Input Client can distribute that message through a central server on the controlling PC to all connected Input Clients on the other controlled PCs. When such other Input Clients are notified about such a condition, they can display a warning on their screen. Because all warnings from all integrated devices can be displayed by all Input Clients, a warning may always be visible on all displays, including the central terminal. The user is therefore informed about warnings from any integrated device, regardless which PC is currently shown on the central terminal.

There can be different levels of how critical or important a warning or an error can be. This allows the user to configure whether he wants to be informed about all warnings and errors detected by the Input Clients or whether he only wants to be informed about really serious problems.

In addition to the above, screen and/or source shots may be obtained. The term "screen shot" as used herein can be understood as being a shot performed by or from an output card. The term "source shot" can be understood as a shot being performed by or from an input card.

The state-of-the-art technology for obtaining screen shots provides only for the possibility of taking single screen shots. In cases where there are more than one monitor connected to a computer or a PC, Microsoft Windows can take one large screen shot that shows all displays together. However, when different screens have different resolutions or different resolution settings, black areas may be formed in the screen shot corresponding to those areas having different resolutions.

A method for taking screen shots and/or source shots of a plurality of images from a plurality of image sources is provided, wherein the shots can be simultaneously initiated, e.g., by a single action of a user while preferably keeping the original resolution and/or size of each image. Thus, screen shots of multiple screens, as well as image stills (also referred to as source shots) of a video source or a computer or PC source can be obtained at the same time. Further, these screen shots or source shots can be obtained before the image is shown on a display. Screen shots and source shots also can be combined and can be taken or initiated simultaneously. A combined screen shot and/or source shot including at least two screen shots, at least two source shots or at least one screen shot and one source shot can be formed, wherein at least 70% and preferably more, e.g., 80% or 90%, of the original resolution, size, and/or color depth of each image or of the respective image source can be maintained, although these separate images may be combined to a single screen and source shot, which can comprise a plurality of different image files.

Screen shots of multiple screens can be taken at the same time. Additionally, the respective screens may be conveniently selected or changed via a central graphical user interface or a video routing hardware 24, as described herein. The user can obtain multiple screen shots from different images sources, computers or PCs that have been simultaneously taken, e.g., exactly at the same time. Within the meaning of the present application, simultaneously can also mean that the time difference between the screen shot and the corresponding source shot has a predetermined given maximum difference, such as for example three frames. Obtaining multiple screen shots at exactly the same time allows an exact alignment of the respective different screen shots.

Preferably, the screens that are to be captured can be selectively chosen and optionally stored, wherein every screen can be stored in a separate image file that has the resolution of the respective screen, so that there are no unused or black areas in the combined shot, even if the respective original images have different screen resolutions.

If one or more source shots are used as image sources, a shot of a video or PC signal can be taken before it is scaled and displayed at the screen. The user, for example, can display four downscaled sources on one screen that does not contain any black areas, while the pictures of all sources can be provided with the original resolution. If screen shots and source shots are combined, the user can automatically be provided with an overview picture and the contained sources in full resolution.

Preferably, the source shot functionality also allows the capture of a source that is not displayed at all on a screen. This functionality, for example, can be used to automatically create image captures of sources for documentation purposes at regular intervals. This automatic documentation is also possible when the respective displays show some other content and can be used for documenting a medical procedure.

A system for performing the method described herein comprises the video processor to which video sources (e.g., microscopes, endoscopes, etc.) and computer or PC sources (e.g., a navigation system or C-arms) can be connected. Additionally, the video processors can provide or have connections to some displays such as, for example, monitors or beamers.

The signal from a connected source can be digitized inside an input card, if necessary, e.g., if the signal from the connected source is an analog signal or the like. The input card can then feed the digitized signal to a proprietary high-speed bus. Then this signal may be received by output cards and displayed on a monitor.

Every output card can perform screen shots simultaneously with other output cards or other screen shots. If there were for example 10 output cards, wherein every card is a dual head card with two independent monitor connectors, a simultaneous screen shot would represent up to 20 pictures at once.

Every input card can perform source shots simultaneously with the others. If there were for example 10 input cards and every card is a dual head card with two independent PC input connections, a simultaneous source shot would represent up to 20 pictures at once. Additionally, there are input cards which can connect twelve video sources instead of two PC sources, so that the number of pictures would increase accordingly.

Both screen shots and source shots can be done simultaneously, wherein a time difference between a screen shot and the corresponding source shot of a given number of frames (e.g., three frames) can be interpreted as being simultaneous, as mentioned above.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A computer network system, comprising:
   a) a controlling PC;
   b) at least one controlled PC controllable by the controlling PC via a data connection including a network, said controlled PC configured to control a medical device;
   c) a plurality of central terminals having a display, wherein different controlled PCs are simultaneously and independently controllable from at least one of the plurality of central terminals; and
   d) a video router operatively coupled to each of the at least one controlled PCs and the at least one central terminal display to transmit video or monitor signals from each of the controlled PCs to the at least one central terminal display along a path separate from the network, wherein control commands from the controlling PC are transmitted to the at least one controlled PC along a path including the network,
      wherein each central terminal includes a user input device communicatively coupled to the controlling PC via a path separate from the at least one controlled PC.

2. A computer network system according to claim 1, wherein the video router is separated from the controlling PC by a predetermined distance.

3. A computer network system according to claim 1, wherein the display is a touch screen, and signals generated at the touch screen are provided to the controlling PC.

4. A computer network system according to claim 1, wherein the central terminal further includes at least one keyboard and/or at least one mouse connected to the controlling PC.

5. A computer network system according to claim 1, wherein at least one of the controlled PCs is operatively coupled to or a part of a medical device.

6. A method for operating a network system including a controlling PC, at least one controlled PC controllable by the controlling PC via a data connection including a network, said controlled PC configured to control a medical device, a plurality of central terminals having a display, and a video router operatively coupled to each of the at least one controlled PCs and the at least one central terminal display, wherein each central terminal includes a user input device communicatively coupled to the controlling PC via a path separate from the at least one controlled PC, comprising:
  transmitting control commands from the controlling PC to the at least one controlled PC along a path including the network, said transmitting control commands including simultaneously and/or independently transmitting control commands to different controlled PCs from at least one of the plurality of central terminals; and
  transmitting video signals from the at least one controlled PC to the central terminal display via the video router along a path separate from the network.

7. The method according to claim 6, further comprising using a software module installed on the at least one controlled PC to implement control commands on the controlled PC, wherein implementing control commands includes generating operating system input events from input events generated at the central terminal display or from devices coupled to the controlling PC.

8. The method according to claim 6, further comprising displaying a graphical user interface in front of all other applications on the central terminal display, wherein said graphical user interface is operable to control each of the at least one controlled PCs.

9. The method according to claim 8, further comprising moving the graphical user interface to a different position on the central terminal display if a part of the display covered by the graphical user interface is designated as being relevant for controlling the respective controlled PC.

10. The method according to claim 6, further comprising detecting and displaying on the central terminal display and/or on displays of the controlled PCs a warning and/or error message transmitted via the network to the controlling PC.

11. The method according to claim 10, wherein detecting includes using pattern recognition to detect the warning and/or error message.

12. The method according to claim 6, further comprising transferring a user interface of the controlled PC to the central terminal display so as to maintain screen content of the controlled PC.

13. The method according to claim 6, further comprising the controlled PC reacting to an output of another controlled PC, said output transferred over the network.

14. The method according to claim 6, further comprising avoiding conflicts arising from user input from several central terminals of the plurality of terminals by indicating user input activity at one central terminal of the plurality of terminals on the other central terminals of the plurality of terminals through a graphical user interface and/or by blocking user input activity at the other central terminals for a specific period of time.

15. The method according to claim 6, further comprising distributing via the video router a video signal to a plurality of central terminals, and each of the plurality of terminals simultaneously display and operate the same controlled PC.

16. A non-transitory computer readable storage medium with an executable program stored thereon for operating a network system including a controlling PC, at least one controlled PC controllable by the controlling PC via a data connection including a network, said controlled PC configured to control a medical device, a plurality of central terminals having a display, and a video router operatively coupled to each of the at least one controlled PCs and the at least one central terminal display, wherein each central terminal includes a user input device communicatively coupled to the controlling PC via a path separate from the at least one controlled PC, and wherein the program instructs a processor to perform the following steps:
  transmitting control commands from the controlling PC to the at least one controlled PC along a path including the network, said transmitting control commands including simultaneously and/or independently transmitting control commands to different controlled PCs from at least one of the plurality of central terminals; and
  transmitting video signals from the at least one controlled PC to the central terminal display via the video router along a path separate from the network.

17. A computer network system according to claim 1, wherein the video or monitor signals are transmitted independent from the data connection.

18. A computer network system according to claim 1, further comprising the network coupled between the controlling PC and the at least one controlled PC.

19. A computer network system, comprising:
  a) a controlling PC;
  b) at least one controlled PC controllable by the controlling PC via a data connection including a network, said controlled PC configured to control a medical device;
  c) a plurality of central terminals having a display, wherein different controlled PCs are simultaneously and independently controllable from at least one of the plurality of central terminals; and
  d) a video router operatively coupled to each of the at least one controlled PCs and the at least one central terminal display to transmit video or monitor signals from each of the controlled PCs to the at least one central terminal display along a path separate from the network,
    wherein each central terminal includes a user input device communicatively coupled to the controlling PC via a path separate from the at least one controlled PC.

20. A computer network system according to claim 19, wherein the data connection including the network spans at least between the controlling PC and the at least one controlled PC, and the video router and the data connection are independent of one another.

21. A computer network system according to claim 1, wherein the data connection including the network spans at least between the controlling PC and the at least one controlled PC, and the video router and the data connection are independent of one another.

22. The method according to claim 6, wherein the data connection including the network spans at least between the controlling PC and the at least one controlled PC, and the video router and the data connection are independent of one another.

23. The method according to claim 1, wherein at least one of the at least one controlled PCs comprises graphical user interface (GUI) logic for generating a GUI configured to monitor and/or control a medical device couple to the at least one controlled PC, the GUI being transmitted as the video or monitor signals.

\* \* \* \* \*